US012544515B2

(12) United States Patent
Dayalan

(10) Patent No.: US 12,544,515 B2
(45) Date of Patent: Feb. 10, 2026

(54) SAFETY SYRINGE WITH ROTATING SLEEVE LOCK

(71) Applicant: Becton, Dickinson and Company, Franklin Lakes, NJ (US)

(72) Inventor: Kathiravan Dayalan, Tiruvallur Dt (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 659 days.

(21) Appl. No.: 18/072,448

(22) Filed: Nov. 30, 2022

(65) Prior Publication Data

US 2024/0173487 A1 May 30, 2024

(51) Int. Cl.
*A61M 5/32* (2006.01)
*A61M 5/31* (2006.01)
*A61M 5/34* (2006.01)

(52) U.S. Cl.
CPC ........ *A61M 5/3243* (2013.01); *A61M 5/3134* (2013.01); *A61M 5/3202* (2013.01); *A61M 5/347* (2013.01)

(58) Field of Classification Search
CPC .............. A61M 5/3243; A61M 5/3134; A61M 5/3202; A61M 5/347
See application file for complete search history.

(56) References Cited

U.S. PATENT DOCUMENTS

| | | | |
|---|---|---|---|
| 4,743,233 A | 5/1988 | Schneider | |
| 4,998,920 A * | 3/1991 | Johnson .............. | A61M 5/3243 604/263 |
| 5,169,392 A | 12/1992 | Ranford et al. | |
| 5,279,584 A | 1/1994 | Dillard, III et al. | |
| 5,713,871 A | 2/1998 | Stock | |
| 6,926,696 B2 | 8/2005 | Mohammed | |
| RE43,834 E | 11/2012 | Steenfeldt-Jensen et al. | |
| 9,586,011 B2 | 3/2017 | Roberts et al. | |
| 10,159,808 B2 | 12/2018 | Samandi et al. | |
| 2012/0277685 A1 | 11/2012 | Limaye | |
| 2015/0126905 A1* | 5/2015 | Lowry ............. | A61B 5/150519 600/576 |
| 2015/0133870 A1 | 5/2015 | Ashworth et al. | |

FOREIGN PATENT DOCUMENTS

WO 2012013585 A1 2/2012

* cited by examiner

*Primary Examiner* — Tasnim Mehjabin Ahmed
(74) *Attorney, Agent, or Firm* — Dickinson Wright PLLC

(57) ABSTRACT

A safety lock syringe assembly comprising a barrel including a distal end and a proximal end, one or more lugs extending outwardly from an outer surface of the barrel, and a needle extending from the distal end, and a sleeve having threads that engage the one or more lugs, the sleeve includes a sleeve locking mechanism, wherein the sleeve threadably rotates in a first direction to a first position that exposes the needle, the sleeve threadably rotates in a second direction to a second position that shields the needle, and the sleeve threadably rotates in the second direction to a third position that engages the one or more lugs to the sleeve locking mechanism to irreversibly lock the shield to the barrel.

20 Claims, 7 Drawing Sheets

SAFETY SYRINGE WITH ROTATING SLEEVE LOCK

FIELD OF THE INVENTION

The present invention relates to medical devices, and more particularly, to medication delivery devices where a stopper or plunger is advanced through a reservoir to dispense medication from the reservoir.

BACKGROUND OF THE INVENTION

A syringe is a pump having a barrel that can contain a fluid, a plunger that moves within the barrel, and a needle for allowing the fluid to be withdrawn from a reservoir and injected into a body during axial movement of the plunger. Syringes are generally stored in sterile environments prior to use to avoid the potential for infection resulting from bacteria or viruses on the needle or in the barrel. Thus, a common concern with syringes is the potential for reuse; reuse of syringes is a common source for bacteria and viruses, such as HIV. A safety syringe is a syringe that is designed to be rendered inoperable after single use to prevent reuse.

Safety syringes come in many varieties, and use many different designs to prevent reuse. Various factors that increase material and labor costs for existing safety pen needles include, for example, the number of components, molding equipment and operation, use of a spring, and secondary post processing operations. Current patient end shielding assemblies involve spring subassemblies and multiple moving parts. For example, many use springs and sleeves, arranged such that, upon performance of a mechanical action to rearrange the syringe, the needle is locked in a position within the sleeve such that the needle cannot extend beyond the sleeve. A disadvantage of safety syringes is that they generally have more parts, and therefore require more material in construction and are more complicated to assemble. Also, many safety syringes have a large barrel for the sleeve and/or a secondary shield. Thus, an improved safety syringe having a reduced number of parts, complexity and material requirements is desired.

SUMMARY OF EMBODIMENTS OF THE INVENTION

Accordingly, it is an aspect of the present invention to provide a safety lock syringe assembly comprising a barrel including a distal end and a proximal end, one or more lugs extending outwardly from an outer surface of the barrel, and a needle extending from the distal end, and a sleeve having threads that engage the one or more lugs, the sleeve includes a sleeve locking mechanism, wherein the sleeve threadably rotates in a first direction to a first position that exposes the needle, the sleeve threadably rotates in a second direction to a second position that shields the needle, and the sleeve threadably rotates in the second direction to a third position that engages the one or more lugs to the sleeve locking mechanism to irreversibly lock the shield to the barrel.

The safety lock syringe assembly disclosed herein advantageously does not involve a secondary shield and does not involve a spring. Moreover, the safety lock syringe assembly includes a revolve lock feature that advantageously involves a threaded sleeve engaging lugs on a barrel to rotationally move into three positions—an injection position, a shielded position and a locked position. Accordingly, the safety lock syringe assembly design disclosed herein has less parts, is less complex and requires less material compared to traditional safety syringes in the art.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, of which.

DETAILED DESCRIPTION OF EMBODIMENTS OF THE PRESENT INVENTION

Figure 1:
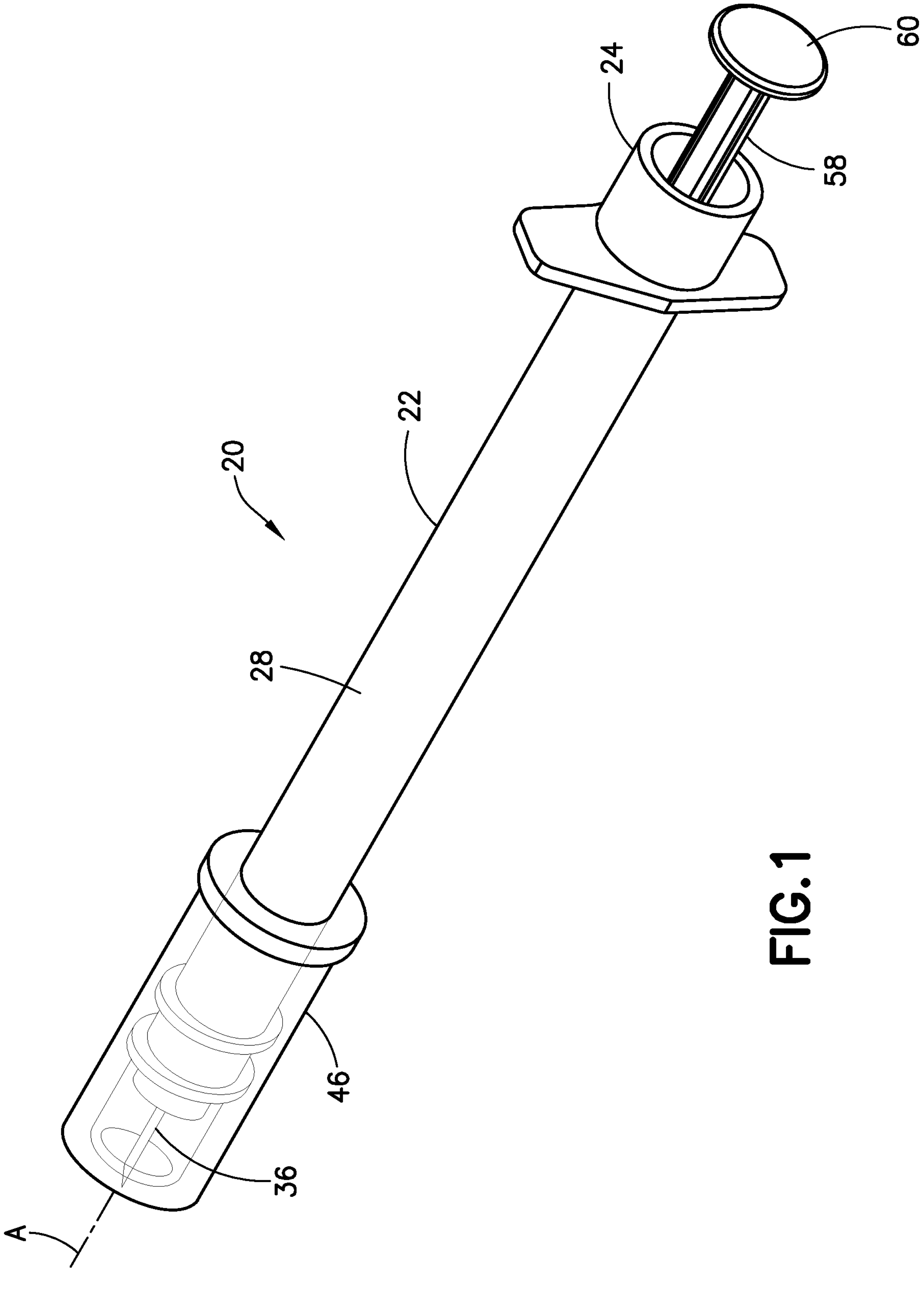
FIG. 1 illustrates a perspective view of a safety lock syringe assembly according to an exemplary embodiment of the present disclosure.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

The embodiments are not intended to be mutually exclusive so that the features of one embodiment can be combined with other embodiments as long as they do not contradict each other.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways.

Phraseology and terminology used herein is for the purpose of description and should not be regarded as limiting. The use of "including," "comprising," or "having" and variations thereof herein is meant to encompass the items listed thereafter and equivalents thereof as well as additional items.

It will be further understood that, although the terms, "first," "second," "third," etc., may be used herein to describe various elements, components, regions, layers and/or sections, these elements, components, regions, layers and/or sections may not be limited by these terms. These terms are only used to distinguish over element, component, region, layer or section from another element, component, region, layer or section.

As used herein, the term "and/or" includes any and all combinations of one or more of the associated listed items. Expressions such as "at least one of," when preceding a list of elements, modify the entire list of elements and do not modify the individual elements of the list. In addition, the terms such as "unit,"-er (-or)," and "module" described in the specification refer to an element for performing at least one function or operation, and may be implemented in hardware.

Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up," "down," "bottom," "top," "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely.

Many of these exemplary embodiments that are obvious to those of ordinary skill in the technical field to which these exemplary embodiments pertain may not be described here in detail. In addition, various features of the exemplary embodiments can be implemented individually or in any combination or combinations, and would be understood by one of ordinary skill in the art of medicament delivery devices.

Figure 2:
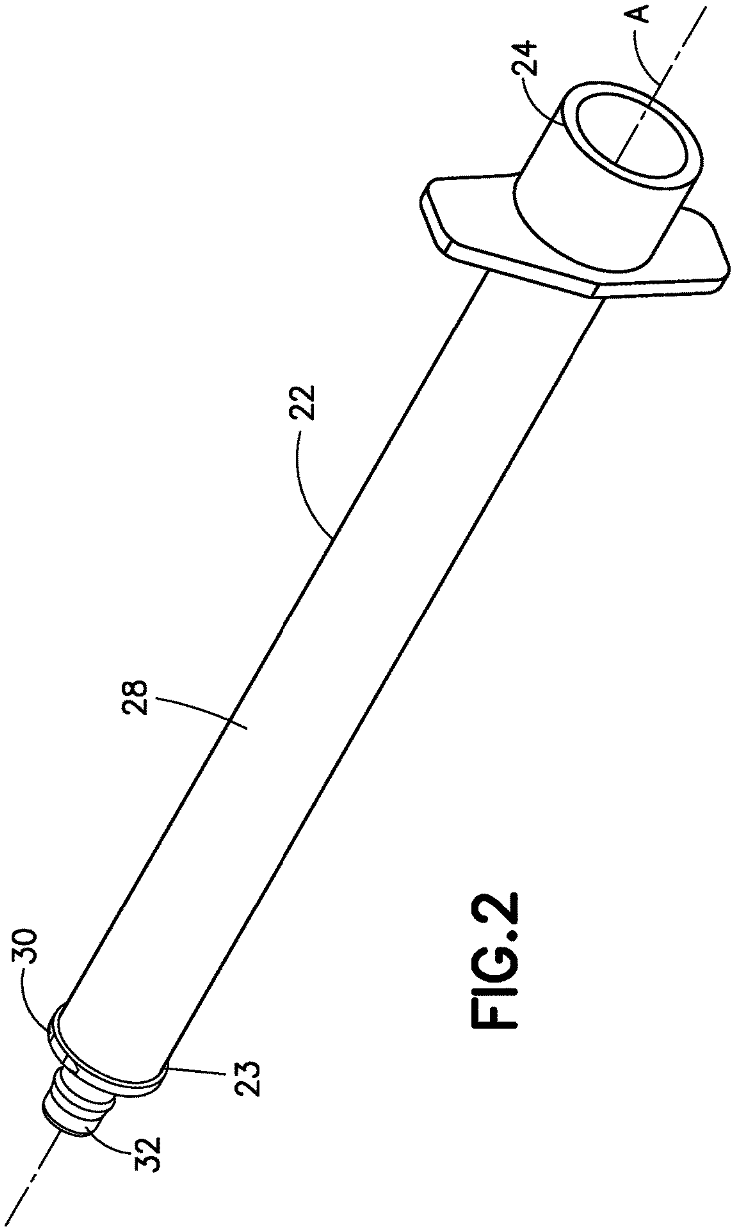
FIG. 2 illustrates a perspective view of a barrel of FIG. 1.
Figure 3B:
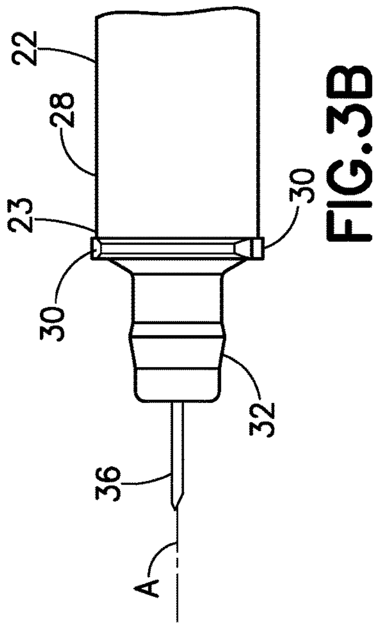
FIG. 3A-3B illustrate partial side views of the barrel of FIG. 1.
Figure 3A:
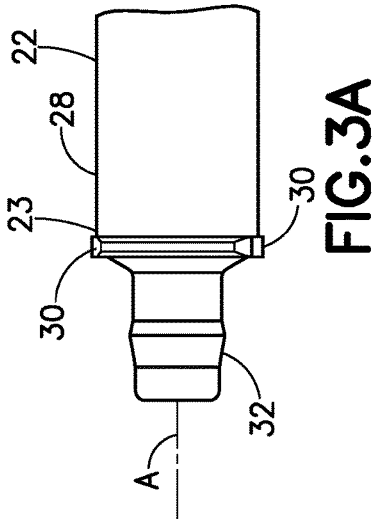
Figure 5:
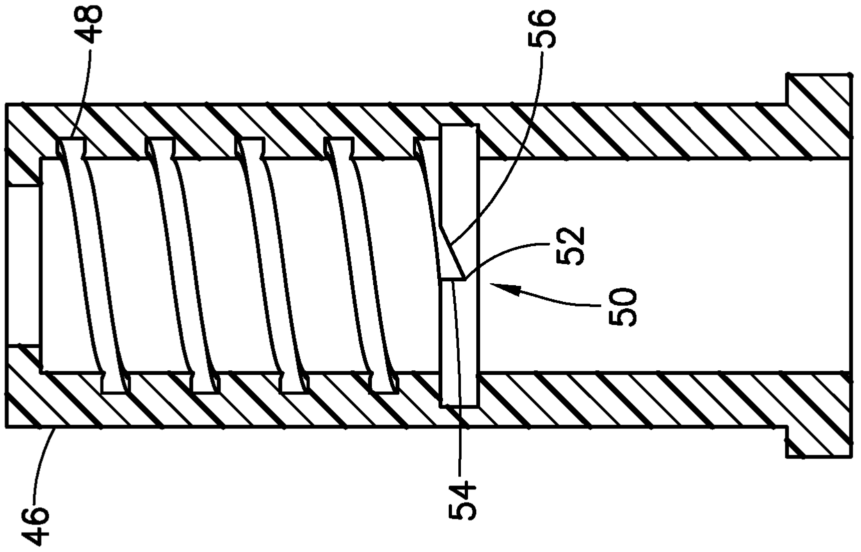
FIG. 5 illustrates a cross-sectional view of the sleeve of FIG. 1.
Figure 4:
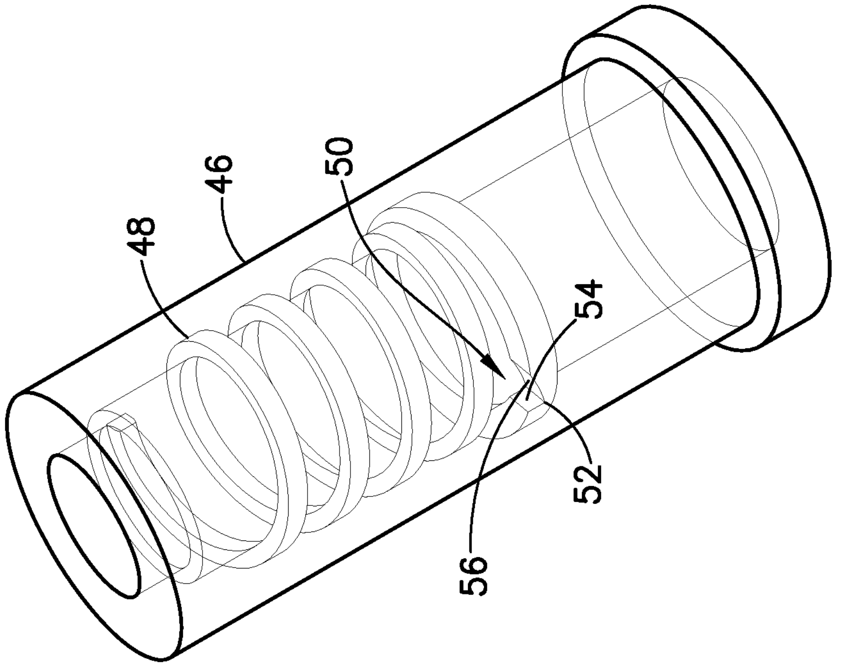
FIG. 4 illustrates a transparent perspective view of a sleeve of FIG. 1.
Figure 6:
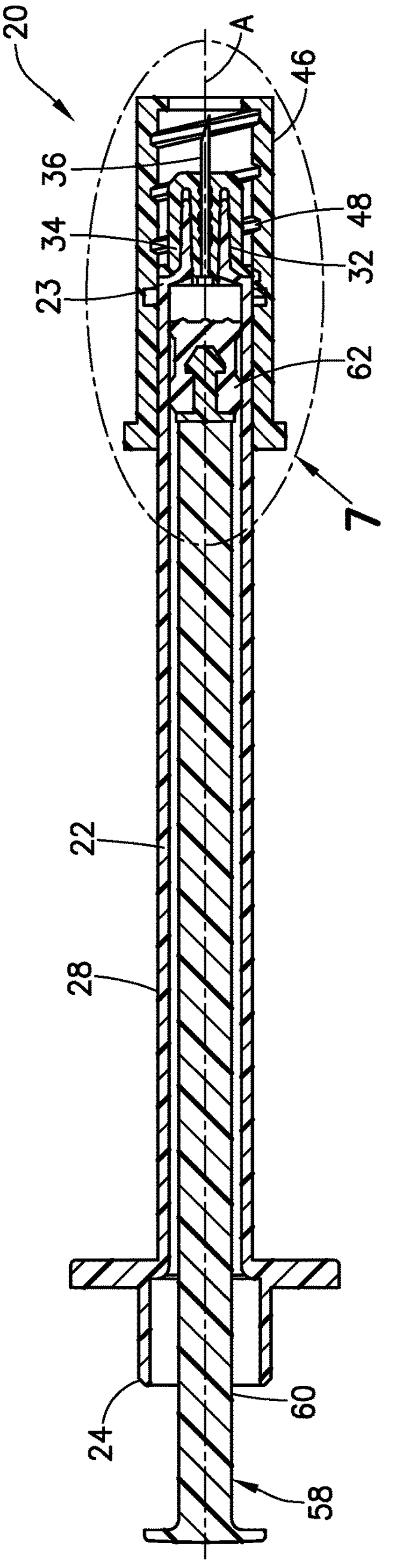
FIG. 6 illustrates a cross-sectional view of the safety lock syringe assembly of FIG. 1 with the sleeve in an initial position.
Figure 7:
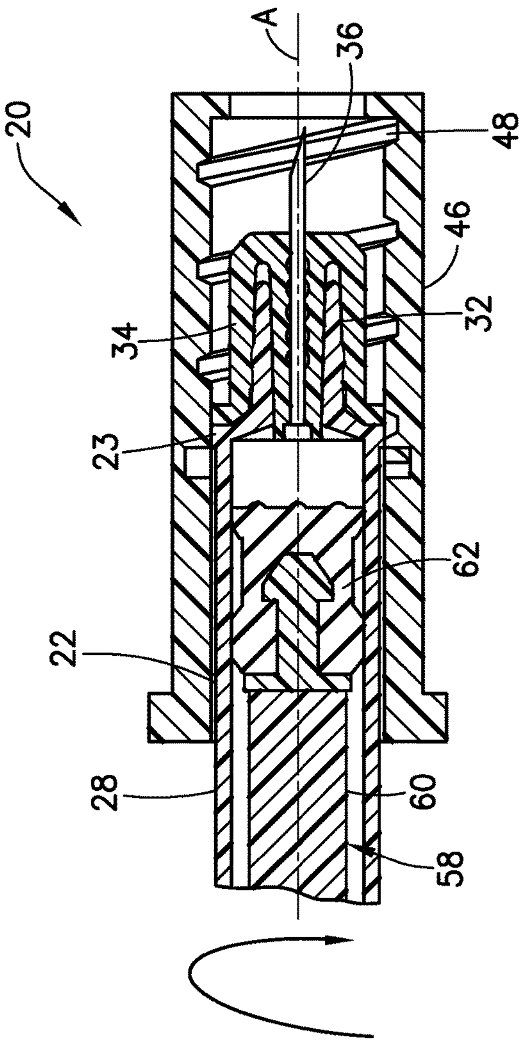
FIG. 7 illustrates a partial cross-sectional view of the safety lock syringe assembly of FIG. 1 with the sleeve in the initial position.
Figure 8:
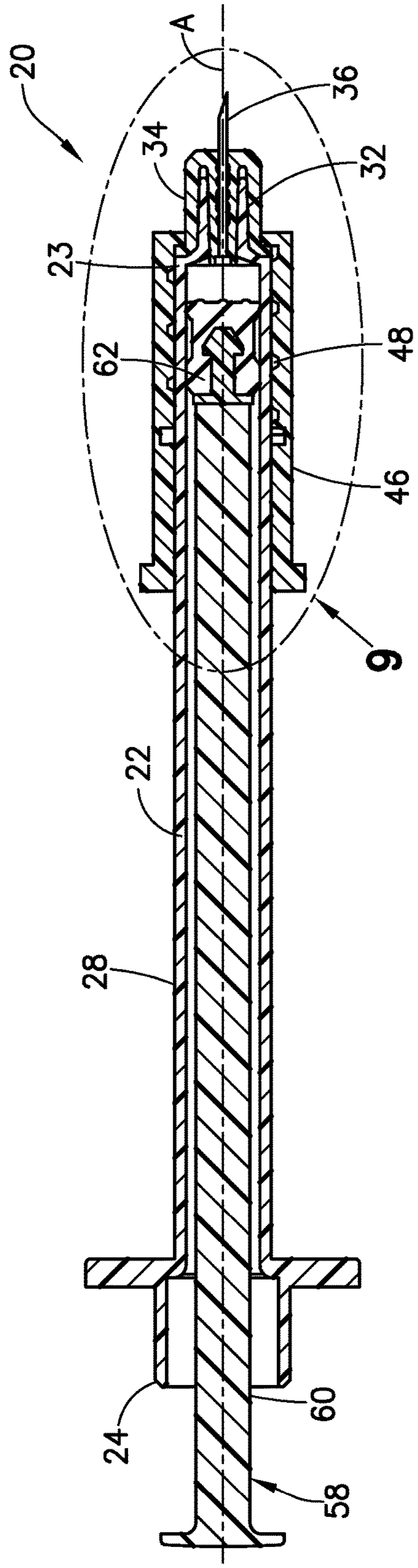
FIG. 8 illustrates a cross-sectional view of the safety lock syringe assembly of FIG. 1 with the sleeve in an injection position.
Figure 9:
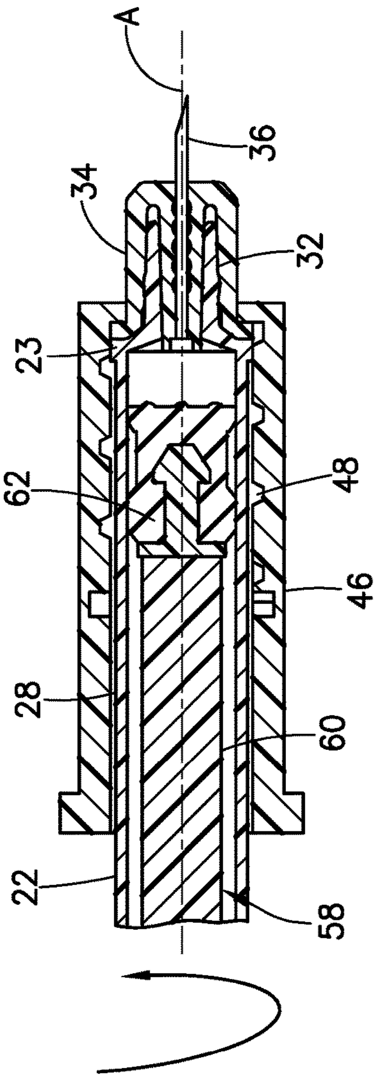
FIG. 9 illustrates a partial cross-sectional view of the safety lock syringe assembly of FIG. 1 with the sleeve in the injection position.
Figure 10:
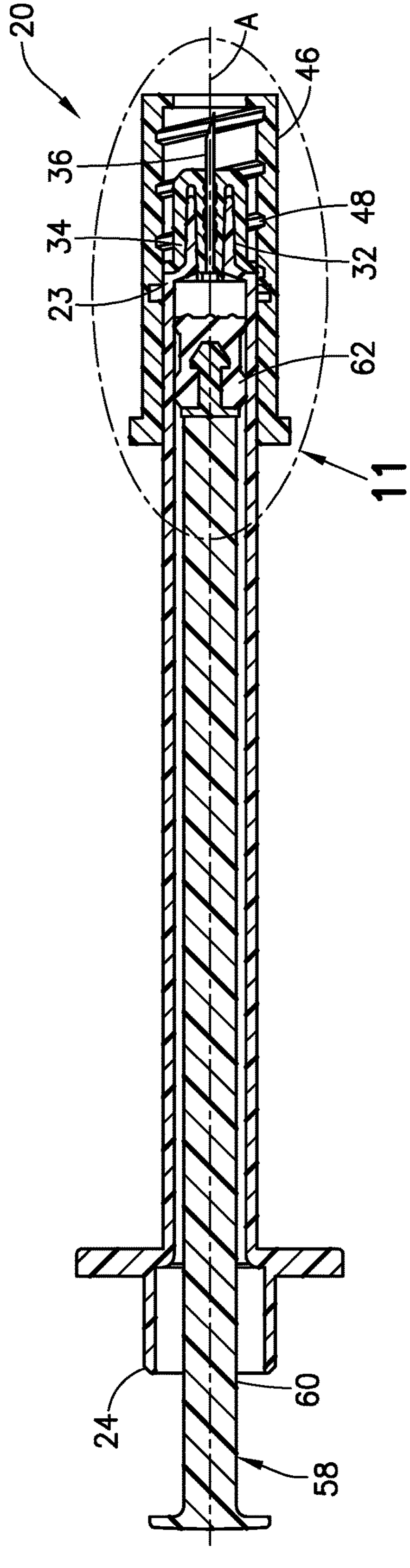
FIG. 10 illustrates a cross-sectional view of the safety lock syringe assembly of FIG. 1 with the sleeve in a shielded position.
Figure 11:
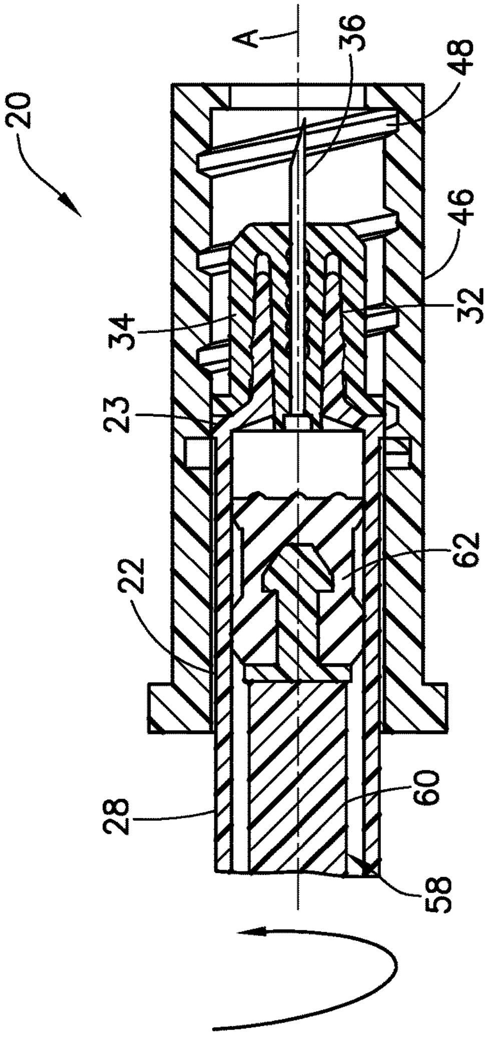
FIG. 11 illustrates a partial cross-sectional view of the safety lock syringe assembly of FIG. 1 with the sleeve in the shielded position.
Figure 12:
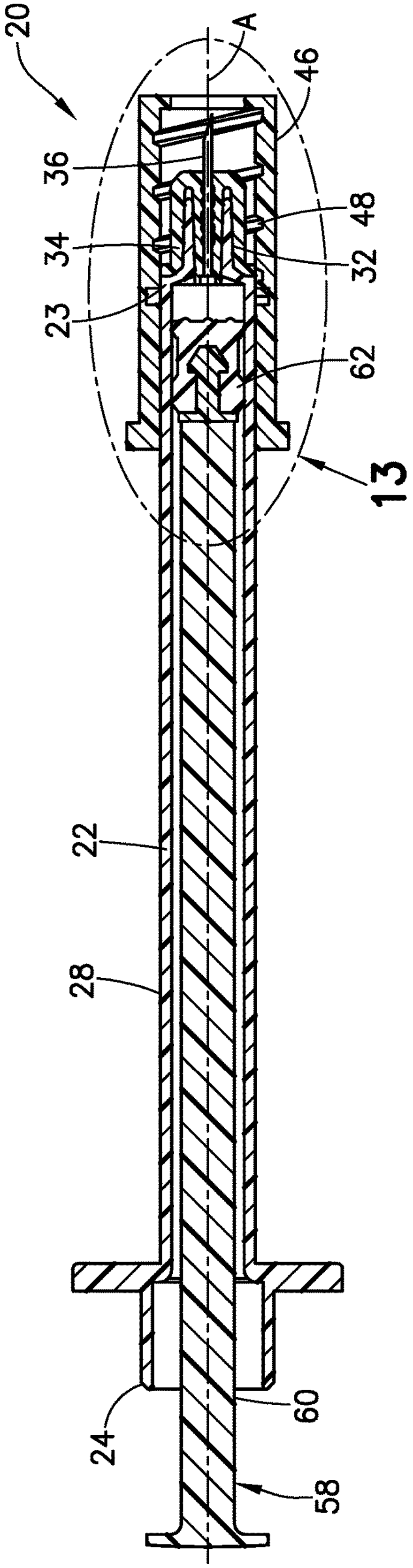
FIG. 12 illustrates a cross-sectional view of the safety lock syringe assembly of FIG. 1 with the sleeve in a locked position.
Figure 13:
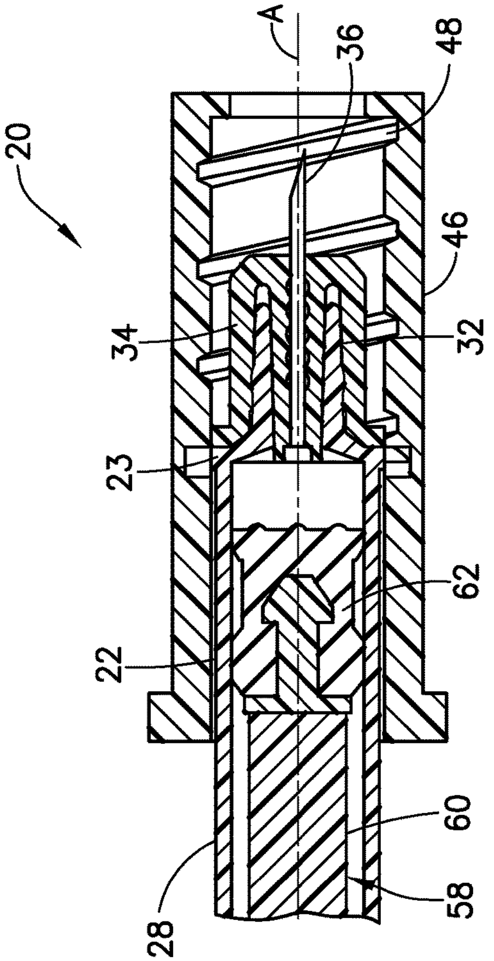
FIG. 13 illustrates a partial cross-sectional view of the safety lock syringe assembly of FIG. 1 with the sleeve in the locked position.

According to an exemplary embodiment, FIGS. 1-13 illustrate a safety lock syringe needle assembly 20 also referred to as a safe revolve syringe. The safety lock syringe needle assembly 20 includes a barrel 22 for containing a medium (e.g., an injectable medication, such as insulin) having a circular cross-section and extending along a longitudinal axis A. As illustrated in FIGS. 2, 3A and 3B, the barrel 22 includes a distal end 23, a proximal end 24 and an exterior surface 28. The barrel 22 further includes one or more lugs 30 extending radially from the exterior surface 28 and opposite from one another at the distal end 23. A barrel tip 32 extends axially from the distal end 23 of the barrel 22 and in fluid communication with the barrel 22.

As illustrated in FIGS. 6-13, a barrel cap 34 is in fitted engagement with the barrel tip 32. A needle 36 extends axially from the barrel cap 34 and is in fluid communication with the barrel tip 43 and the barrel 22. The needle 36 allows for the medium to be drawn into and/or expelled from the barrel 22. Alternatively, the needle 36 extends directly from the distal end 23 of the barrel 22, as seen in FIG. 3B.

FIGS. 1 and 4-13 illustrate a sleeve 46 that is disposed partially about the distal end 23 of the barrel 22 and the barrel cap 34. The sleeve 46 is configured to prevent needle sticks and inadvertent injections when the sleeve 46 is in a shielded or locked position. The sleeve 46 includes one or more internal threads 48 disposed at a distal portion of the sleeve 46 whereby the one or more internal threads 48 is in threaded engagement with the one or more lugs 30. The engagement between the internal threads 48 and the one or more lugs 30 advantageously provides rotational movement of the sleeve between three positions—an injection position, a shielded position and a locked position.

The sleeve 46 advantageously includes at least one sleeve lock mechanism 50 threadably disposed at a proximal end of the internal threads 48 and disposed at a central portion of the sleeve 46. The sleeve lock mechanism 50 is configured to irreversibly engage with the at least one lug 30 when pressed into contact (engagement) with the at least one lug 30. The at least one sleeve lock mechanism 50 includes a sleeve indentation 52 (or a recess) defined in the sleeve 46 for receiving the at least one lug 30. The sleeve indentation 52 includes a sleeve lock surface 54 parallel to the longitudinal axis A, as well as a sloped sleeve ramp surface 56.

Additionally, the sleeve lock mechanism 50 is advantageously threaded at a different pitch/lead than the remaining internal thread 48 of the sleeve 46. Specifically, the sloped sleeve ramp surface 56 of the sleeve lock mechanism 50 is at a different pitch/lead from the internal thread 48. The sloped sleeve ramp surface 56 provides a continuous travel path between the internal threads 48 and the threads of the sleeve lock mechanism 50 for the lug 30 to enter into the sleeve lock mechanism 50. However, the sleeve indentation 52 and the sleeve lock surface 54 provides an inflection point in the travel path. This inflection point maintains a travel path for the lug 30 to enter into the sleeve lock mechanism 50 but prevents the lug 30 from exiting the sleeve locking mechanism 50 to avoid unlocking. As such, the sleeve lock mechanism 50 advantageously provides for smooth locking engagement motion of the sleeve 46 and avoids unlocking of the sleeve 46 when it is locked via the sleeve lock mechanism 50 by a user.

The safety lock syringe assembly 20 advantageously does not involve a secondary shield in addition to the sleeve 46. Moreover, the safety lock syringe assembly 20 advantageously does not involve a spring. For example, no spring is used to move the sleeve 46 or activate the sleeve lock mechanism 50. Instead, the sleeve 46 advantageously includes the internal threads 48 and the sleeve lock mechanism 50 that engage the lug 30 of the barrel 22 to expose, retract and lock the needle. Accordingly, the design of the safety lock syringe assembly 20 disclosed herein advantageously has less parts, is less complex and requires less material compared to traditional safety syringes in the art.

In an alternate embodiment, the at least one thread is disposed on an exterior surface of the barrel and the at least one lug extends inward within the sleeve to provide threaded engagement with the at least one thread (not illustrated). For example, the sleeve includes one or more lugs extending radially inward and opposite from one another. The exterior surface of the barrel includes one or more external threads each in threaded engagement with one of the one or more lugs.

In this alternate embodiment, the barrel includes at least one barrel lock mechanism (similar to the sleeve lock mechanism described above) configured to irreversibly engage with the at least one lug when pressed into contact with the at least one lug (not illustrated). The at least one barrel lock mechanism includes a barrel indentation defined in the exterior surface of the barrel for receiving the at least one lug. The barrel indentation includes a barrel lock surface parallel to the longitudinal axis A, as well as a sloped barrel ramp surface.

Below describes the operation of the exemplary embodiment of the safety lock syringe needle assembly 20. Rotation of the sleeve 46 in a first rotational direction (e.g., clockwise) from an initial position (best illustrated in FIGS. 6 and 7) relative to the barrel 22 moves the sleeve 46 axially along the longitudinal axis A toward the proximal end 24 of the barrel 22 to expose the needle 36 in an injection position (best shown in FIGS. 8 and 9). Rotation of the sleeve 46 takes place via the engagement of the internal threads 48 of the sleeve 46 and the lugs 30 of the barrel 22. In the initial position, the needle 36 is in a shielded sterile state and ready for use. In the injection position, the needle 36 extends out of the sleeve 46 and is ready to expel medicament from the barrel 22 or to draw medicament into the barrel 22.

From the injection position, rotation of the sleeve 46 in a second rotational direction (e.g., counterclockwise) opposite the first rotational direction moves the sleeve 46 axially along the longitudinal axis to return to a shielded position (best illustrated in FIGS. 10 and 11) where the needle 36 is no longer exposed. Rotation of the sleeve 46 takes place via the engagement of the internal threads 48 of the sleeve 46 and the lugs 30 of the barrel 22. The shielded position is similar to the initial position of the needle 36 where the needle 36 is retracted in the sleeve 46.

Further rotation of the sleeve 46 in the second rotational direction moves the sleeve 46 to the locked position (best illustrated in FIGS. 12 and 13) to press the at least one sleeve lock mechanism 50 into contact with the at least one lug 30. As the sleeve 46 approaches the locked position, resistance to rotation increases, until the at least one sleeve lock mechanism 50 "snaps" irreversibly into contact with the at least one lug 30. This resistance may be useful in preventing premature entry of the sleeve 46 into the locked position, thus avoiding waste.

Operation of the alternate embodiment described above is similar to the exemplary embodiment of the safety lock syringe needle assembly 20 disclosed herein. Specifically, rotation of the sleeve in a first rotational direction (e.g., clockwise) from an initial position relative to the barrel moves the sleeve axially along the longitudinal axis A toward the proximal end of the barrel to expose the needle in an injection position. From the injection position, rotation of the sleeve in a second rotational direction (e.g., counterclockwise) opposite the first rotational direction moves the sleeve axially along the longitudinal axis to return to a shielded position where the needle is no longer exposed. Further rotation of the sleeve in the second rotational direction moves the sleeve to a locked position to press the at least one barrel lock mechanism into contact with the at least one lug. As the sleeve approaches the locked position, resistance to rotation increases, until the at least one barrel lock mechanism "snaps" irreversibly into contact with the at least one lug. This resistance may be useful in preventing premature entry of the sleeve into the locked position, thus avoiding waste.

As best shown in FIGS. 1 and 6-13, the safety lock syringe needle assembly 20 further includes a plunger assembly 58. The plunger assembly 58 includes a plunger 60 slideably disposed at least partially within the barrel 22 and a stopper 62 fixed to the plunger 60 and in sealed engagement with the barrel 22. Movement of the plunger assembly 58 along the longitudinal axis A allows for medium to be alternatively pulled into or expelled from the barrel 22.

Although only a few embodiments of the present invention have been shown and described, the present invention is not limited to the described embodiments. For example, different shapes and forms of the sleeve lock feature may be used. Generally, for example, non-circular barrel cross-sections may be employed to optimize space utilization and tailor device size to best suit user comfort. It will be appreciated by those skilled in the art that other changes may also be made to the disclosed embodiments without departing from the scope of the invention. In addition, any of the embodiments, features and/or elements disclosed herein may be combined with one another to form various additional combinations not specifically disclosed, as long as the embodiments, features and/or elements being combined do not contradict each other. All such changes and combinations are considered to be within the scope of the invention as defined by the appended claims and their equivalents. Unless the language "means for" is used, no language in the specification or the claims is intended to invoke 35 U.S.C. 112(f).

What is claimed is:

1. A safety lock syringe assembly comprising:
- a barrel including:
  - a distal end and a proximal end;
  - one or more lugs extending outwardly from an outer surface of the barrel; and
  - a needle extending from the distal end; and
- a sleeve having threads that engage the one or more lugs, the sleeve includes a sleeve locking mechanism; wherein
- the sleeve threadably rotates in a first direction to a first position that exposes the needle;
- the sleeve threadably rotates in a second direction to a second position that shields the needle;
- the sleeve threadably rotates in the second direction to a third position that contacts the one or more lugs to the sleeve locking mechanism to irreversibly lock the sleeve to the barrel; and
- the sleeve locking mechanism includes threads that have a pitch different from a pitch of the threads of the sleeve.

2. The safety lock syringe assembly of claim 1, wherein the one or more lugs are disposed at the distal end of the barrel.

3. The safety lock syringe assembly of claim 1, wherein the one or more lugs includes two lugs that extend radially from an external surface of the barrel and opposite from each other at a distal end of the barrel.

4. The safety lock syringe assembly of claim 1, wherein
- the distal end of the barrel is connected to and in fluid communication with a barrel tip;
- a barrel cap is fixed onto the barrel tip; and
- the needle is fixed to the barrel cap and in fluid communication with the barrel tip.

5. The safety lock syringe assembly of claim 1, wherein the threads of the sleeve are disposed at a distal portion of the sleeve.

6. The safety lock syringe assembly of claim 1, wherein the threads of the sleeve are internal threads.

7. The safety lock syringe assembly of claim 1, wherein the sleeve locking mechanism is disposed at a central portion of the sleeve.

8. The safety lock syringe assembly of claim 1, wherein the sleeve locking mechanism includes a sleeve indentation, a sleeve lock surface and a sloped sleeve ramp surface.

9. The safety lock syringe assembly of claim 1, wherein the sleeve locking mechanism is disposed at a proximal end of the threads of the sleeve.

10. The safety lock syringe assembly of claim 1, wherein the first direction is opposite the second direction.

11. The safety lock syringe assembly of claim 1, further comprising a plunger assembly including:

a plunger slidably disposed in the barrel; and a stopper disposed at a distal end of the plunger to dispense medicament out of the barrel.

12. The safety lock syringe assembly of claim 1, wherein movement between the first, second and third positions occur without use of a spring.

13. The safety lock syringe assembly of claim 1, wherein the sleeve axially moves as a result of rotational engagement between the threads of the sleeve and the one or more lugs of the barrel.

14. The safety lock syringe assembly of claim 1, wherein the one or more lugs is integrally formed to the barrel as a unitary structure.

15. The safety lock syringe assembly of claim 1, wherein the sleeve lock mechanism is configured to irreversibly engage with the one or more lugs when pressed into contact.

16. A safety lock syringe assembly comprising:

a barrel including:

a distal end and a proximal end;

one or more lugs extending outwardly from an outer surface of the barrel; and a needle extending from the distal end; and a sleeve having threads that engage the one or more lugs, the sleeve includes a sleeve locking mechanism; wherein the sleeve threadably rotates in a first direction to a first position that exposes the needle;

the sleeve threadably rotates in a second direction to a second position that shields the needle, the sleeve threadably rotates in the second direction to a third position that contacts the one or more lugs to the sleeve locking mechanism to irreversibly lock the sleeve to the barrel, wherein the sleeve locking mechanism includes a sleeve indentation having a sloped sleeve ramp surface providing a continuous travel path for the one or more lugs and cooperating with a sleeve lock surface.

17. The safety lock syringe assembly of claim 16, the sleeve indentation and the sleeve lock surface provides an inflection point as the one or more lugs engage the sleeve locking mechanism.

18. The safety lock syringe assembly of claim 16, wherein the sleeve lock surface is parallel to a longitudinal axis.

19. The safety lock syringe assembly of claim 16, wherein the sloped sleeve ramp provides a continuous travel path for the one or more lugs to engage the sleeve indentation; and the sleeve indentation cooperates with the sleeve lock surface to prevent the one or more lugs from exiting a locked position.

20. The safety lock syringe assembly of claim 16, wherein the sloped sleeve ramp is at a different pitch from the threads of the sleeve.

* * * * *